(12) United States Patent
Ziegler

(10) Patent No.: US 8,057,437 B2
(45) Date of Patent: Nov. 15, 2011

(54) RADIALLY SEALING VAVLE FOR AN INFUSION SET

(75) Inventor: John S. Ziegler, Arlington Heights, IL (US)

(73) Assignee: Hospira, Inc., Lake Forest, IL (US)

( * ) Notice: Subject to any disclaimer, the term of this patent is extended or adjusted under 35 U.S.C. 154(b) by 321 days.

(21) Appl. No.: 12/194,819

(22) Filed: Aug. 20, 2008

(65) Prior Publication Data

US 2009/0062738 A1 Mar. 5, 2009

Related U.S. Application Data

(60) Provisional application No. 60/969,237, filed on Aug. 31, 2007.

(51) Int. Cl.
*A61M 1/00* (2006.01)
(52) U.S. Cl. .......................... 604/152; 604/151
(58) Field of Classification Search .............. 604/151, 604/152, 247, 288.03
See application file for complete search history.

(56) References Cited

U.S. PATENT DOCUMENTS

| 4,223,813 | A | 9/1980 | Garrett et al. |
|---|---|---|---|
| 4,468,222 | A | 8/1984 | Lundquist |
| 4,696,671 | A | 9/1987 | Epstein et al. |
| 4,828,545 | A | 5/1989 | Epstein et al. |
| 4,846,636 | A | 7/1989 | Danby et al. |
| 4,865,584 | A | 9/1989 | Epstein et al. |
| 4,947,856 | A | 8/1990 | Beard |
| 5,085,644 | A | 2/1992 | Watson et al. |
| 5,113,904 | A | 5/1992 | Aslanian |
| 5,152,753 | A | 10/1992 | Laguette et al. |
| 5,462,256 | A | 10/1995 | Minick et al. |
| 5,465,938 | A | 11/1995 | Werge et al. |
| 5,554,112 | A | 9/1996 | Walbrink et al. |
| 5,584,671 | A | 12/1996 | Schweitzer, Jr. et al. |
| 5,586,868 | A | 12/1996 | Lawless et al. |
| 5,718,569 | A | 2/1998 | Holst |
| 5,740,810 | A | 4/1998 | Johnson et al. |
| 5,755,683 | A | 5/1998 | Houle et al. |
| 5,772,637 | A | 6/1998 | Heinzmann et al. |
| 5,816,779 | A | 10/1998 | Lawless et al. |
| 6,106,498 | A | 8/2000 | Friedli et al. |
| 6,165,154 | A | 12/2000 | Gray et al. |
| 6,210,361 | B1 | 4/2001 | Kamen et al. |
| 6,364,857 | B1 | 4/2002 | Gray et al. |
| 6,390,120 | B1 | 5/2002 | Guala |
| 6,409,707 | B1 | 6/2002 | Guala |
| 6,464,667 | B1 | 10/2002 | Kamen et al. |
| 6,488,652 | B1 | 12/2002 | Weijand et al. |
| 6,494,694 | B2 | 12/2002 | Lawless et al. |
| 6,537,258 | B1 | 3/2003 | Guala |
| 6,672,561 | B2 | 1/2004 | Kerg et al. |
| 6,709,417 | B1 | 3/2004 | Houle et al. |

(Continued)

FOREIGN PATENT DOCUMENTS

WO 02/87664 7/2002

*Primary Examiner* — Nicholas D Lucchesi
*Assistant Examiner* — Victoria P Campbell
(74) *Attorney, Agent, or Firm* — Michael R. Crabb

(57) ABSTRACT

A radially sealing valve for preventing free flow from an IV set has an elastomeric cup portion that covers an outlet opening and is normally closed by its resiliency. The valve can be incorporated into a cassette for an IV pump that automatically opens the valve when the cassette is loaded. Axial force on the bottom of the cupped valve provides radial contraction or expansion of the sidewall of the valve to open a fluid path.

3 Claims, 12 Drawing Sheets

U.S. PATENT DOCUMENTS

| | | |
|---|---|---|
| 6,726,656 B2 | 4/2004 | Kamen et al. |
| 6,755,391 B2 | 6/2004 | Newton et al. |
| 6,905,314 B2 | 6/2005 | Danby |
| 6,942,473 B2 | 9/2005 | Abrahamson et al. |
| 6,942,636 B2 | 9/2005 | Holst et al. |
| 7,004,727 B2 | 2/2006 | Kline et al. |
| 2001/0007932 A1 | 7/2001 | Kamen et al. |
| 2002/0004015 A1 | 1/2002 | Carlisle et al. |
| 2004/0176724 A1 | 9/2004 | Kamen et al. |
| 2006/0030821 A1 | 2/2006 | Lee et al. |
| 2006/0241550 A1 | 10/2006 | Kamen et al. |
| 2008/0208103 A1 | 8/2008 | Demers et al. |

RADIALLY SEALING VAVLE FOR AN INFUSION SET

CROSS-REFERENCE TO RELATED APPLICATIONS

This application claims priority based upon U.S. Provisional Application Ser. No. 60/969,237 filed Aug. 31, 2007, which is expressly incorporated herein by reference in its entirety.

FIELD OF THE INVENTION

The present invention generally relates to controlling flow for infusing a medicinal fluid into a patient. More specifically, the present invention relates to a normally closed radially sealing valve that can be used to prevent free flow from an infusion set. The valve can stand alone or can be incorporated into a cassette that is inserted into a medical pump. The cassette has an elastomeric membrane sandwiched between a front and rear housing, so that displacement of the membrane into a pumping chamber formed in the cassette forces fluid to flow through the cassette and into the patient.

BACKGROUND OF THE INVENTION

Cassette pumps provide a convenient and relatively low cost device for infusing drugs into the body of a patient. These pumps employ intravenous or IV sets that have pump cassettes made of injection molded plastic, which are discarded after use with a patient. A pump designed to operate with a particular configuration of cassette includes a drive mechanism that actuates the cassette to deliver fluids to a patient. Such pumps are typically controlled by a microprocessor that can be programmed to deliver a predefined volume of medicinal fluid, at a predefined rate, and over a predefined time. Cassette pumps are typically more accurate than peristaltic pumps and are able to deliver drugs at a relatively wide range of rates and volumes.

In a cassette pump disclosed in U.S. Pat. No. 4,865,584, which is assigned to the same assignee as the present invention, the cassette comprises a housing having a front portion that includes openings for valve actuators and a pump plunger, and a rear portion in which passages, valve seats, and a pumping chamber are formed. An elastomeric membrane is sealed between the front and rear portions of the cassette body. The elastomeric membrane seals the passages formed in the rear portion and is displaced by the valve actuators to close valves formed in the housing and by a pump plunger to force fluid through the cassette. Said valves are normally open when outside the pump and are closed by actuators in the pump. The fluid enters the cassette housing through either a primary or a secondary inlet port and is forced through an outlet port under pressure. During an intake stroke, the outlet valve closes, the inlet valve opens, and the pump plunger draws back. The fluid is then drawn through the open inlet valve and into the pumping chamber as the elastomeric membrane covering the pumping chamber pulls back from its prior fully displaced configuration. In a pumping stroke, the inlet valve closes, the outlet valve opens, and the pump plunger forces the elastomeric membrane back into the pumping chamber to force the fluid contained therein through the outlet port.

One problem with the IV set, cassette and pump described in the '584 patent is that free flow of fluid may occur at any time the cassette is not secured in the pump with the outlet valve closed. Free flow is undesirable when the infusion set containing the cassette is fluidly connected to an IV bag containing a drug and the patient because an overdose of the drug can result. If free flow occurs before the cassette is inserted into the pump or connected to the patient, then some of the contents of the IV bag are spilled or lost. This can result in under-delivery of the drug if all of the bag's contents were supposed to be delivered. However, selective free flow of fluid through the cassette would be desirable for manually priming the infusion set with fluid to remove any air before the cassette of the set is inserted into the pump or connected to the patient.

Additionally, in order to avoid causing air embolisms in the patient's blood vessels, conventional procedures require a user of the pump described in the '584 patent to install the cassette in the pump and then perform a special automatic priming procedure using the pumping mechanism to purge the line of air before the set is connected to the patient. It would be advantageous if the user had the flexibility to choose between manual priming, automatic priming or some combination of both to meet their needs, save time or better utilize the pump. A valve or cassette that provides both anti-free flow and priming functions with or without being installed in a pump is needed.

Thus, there is a need in the art for an infusion set with a selectively openable valve that is normally closed and does not have to be closed by a pump mechanism. There is a need for a valve that is always in a closed position until connecting to the pump at which time the valve is automatically opened. Additionally there is a need for an economical cassette with a simplified design compared to the state of the art. Also, improved integrity of a valve that prevents flow through a cassette is desired. Further, elimination of precise control in aligning pieces of the cassette during manufacturing is desired to minimize manufacturing costs.

Thus, a principal object of the present invention is to prevent free-flow when a cassette or IV set is not installed in a pump.

Another object of the present invention is to provide an improved cassette for an intravenous pump, wherein the cassette has a normally closed valve that is automatically opened when the cassette is securely installed in the pump.

Another object of the present invention is to provide a valve or cassette that provides both anti-free flow and priming functions with or without being installed in a pump.

Another object of the present invention is to provide a valve or cassette that gives the user the flexibility to choose between manual priming, automatic priming or some combination of both to meet their needs, save time, or better utilize a pump.

Another object of the present invention is to provide a valve that acts as a pressure actuated check valve.

Another object of the present invention is to provide a valve that acts as a pressure relief valve.

Another object of the present invention is to provide a valve that acts as a pressure actuated check valve in one direction of fluid flow and a pressure relief valve in an opposite direction of fluid flow.

Another object of the present invention is to provide a simplified design for a cassette to minimize costs.

Another object of the present invention is to provide a simplified design for a valve to minimize costs.

These and other objects, features, or advantages will become apparent from the specification and claims.

BRIEF SUMMARY OF THE INVENTION

In accordance with the present invention, a normally closed radially sealing valve that can be used to prevent free flow from an infusion set is provided. The valve can be incorporated into an IV set or a cassette that is inserted into a medical pump.

In one aspect of this invention, a cassette includes a housing having an inlet port and an outlet port, and the housing has a front portion and a rear portion between which is sealed an elastomeric membrane that cooperates with the housing to define a fluid path within the housing between the inlet port and the outlet port. A valve is provided in a fluid path between the inlet port and the outlet port and is a cupped member formed in the elastomeric membrane that is inserted into an opening of a chamber within the housing. Specifically, the cup member is resilient and has a cross section greater than the cross section of the opening such that when the cup member is inserted into the opening of the chamber the cup closes, seals, or occludes the opening and thus closes, seals, or occludes the fluid path. Thus, the valve is in a normally closed position.

When connecting the cassette to the pump an actuating member engages the cup member to expand the cup member axially and in turn radially contract the sidewalls of the cup member away from the walls of the housing to allow the fluid path to be opened within the opening. In this manner the cup functions as an anti-free flow valve. The valve can also act as a priming valve, which can be actuated outside of the pump by pressing on the actuating member.

In another aspect of the present invention the anti-free flow valve operates as a check valve. In this aspect the housing has a first port that is in fluid communication with the top portion of the anti-free flow valve and a second port in fluid communication with the sidewall of the anti-free flow valve. Thus fluid pressure within the first port is transmitted to the top portion of the anti-free flow valve causing expansion of the sidewall radially to strengthen the seal of the sidewall against the second port. Therefore, flow can only occur when the pressure in the second port exceeds the pressure in the first port by a threshold amount, and flow can only occur from the second port to the first port.

In yet another aspect, the present invention is directed to another cassette pump for delivering medicinal fluid to a patient. The cassette pump employes a cassette like that described in the preceding paragraphs. The anti-free flow valve again has an elastomeric membrane with a cup member with a greater cross section than the outlet valve opening. In this aspect the cup member surrounds and engages the sidewall of the outlet valve opening wherein the resilience of the cup member creates a bias seal between the cup member and the sidewall.

When the cassette is inserted into the pump, a pin distorts the elastomeric membrane to move the cup member away from the sidewall of the outlet valve opening, thus allowing the medicinal fluid to flow through (e.g., pass around) the anti-free flow valve. Again, the valve can act as a priming valve, which can be actuated outside of the pump by pressing on the actuating member.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings.

DETAILED DESCRIPTION OF THE PREFERRED EMBODIMENT(S)

Figure 1:
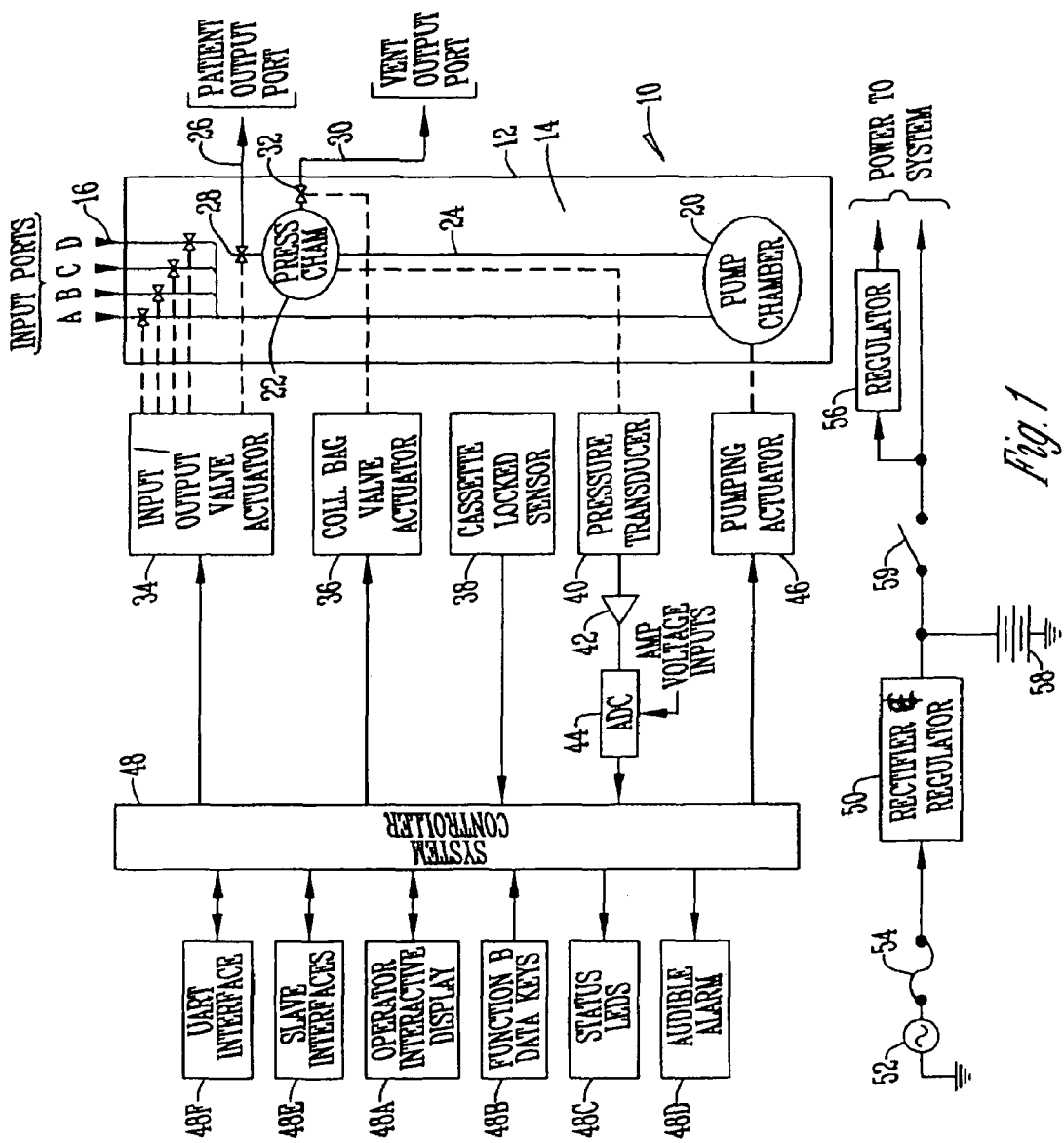
FIG. 1 is a block diagram of the cassette pump, illustrating the functional components of the pump and the cassette.

FIG. 1 is a block diagram illustrating the functional components of an intravenous (IV) pump 10, which is used in connection with a disposable cassette 12 for intravenously delivering a medicinal fluid to a patient. Cassette 12 includes a housing 14 on which is disposed one or more inlet ports 16 for accepting the medicinal fluid flowing from an IV bag or other fluid container (not shown) through fluid lines that couple the source of medicinal fluid to the inlet port of cassette 12 (also not shown). Similarly, fluid lines (not shown) couple an outlet port 18 (FIG. 2) on housing 14 to the body of a patient. Details of pump 10 that are not discussed below can be determined by reference to commonly assigned U.S. Pat. No. 4,865,584, the disclosure and drawings of which are hereby specifically incorporated herein by reference. Where differences exist between the present invention and the prior art pump disclosed in this reference, the following discussion provides an enabling disclosure that should be relied upon instead of the disclosure in the referenced patent.

The cassette 12 includes a pumping chamber generally designated 20 connected to the fluid channel, and a pressure chamber generally designated 22 connected to the pumping chamber 20 via a fluid flow channel 24. A patient output port 26 is connected in a fluid flow path to the pressure chamber 22 via a valve 28, and a vent output port 30 is connected to the pressure chamber 22 in a fluid flow path via a valve 32. The patient output port 26 is directly connectable to a patient via a patient output line, not shown. The vent output port 30 is directly connectable, for example, to a collection bag or other fluid sink.

An input and output valve actuator 34 is operatively connected to the plural fluid input valves and to the patient output valve 28. The actuator 34 is operative to select the "open" and the "closed" state of the valves 28, and therewith to control fluid flow from the corresponding fluid input ports 16 into the cassette 12 and to control fluid flow out of the cassette into the patient. The actuator 34 is preferably operative to prevent the input and output valves from being simultaneously in the "open" condition to eliminate the possibility of unintended gravity flow infusion (also known as "free flow"). A separate actuator is preferably connected to the output valve 28 to maintain the patient output port and any selected input port "open".

A vent valve actuator 36 is operatively connected to the vent valve 32. The actuator 36 is operative to select the "open" and the "closed" state of the valve 32, and therewith to control fluid flow from the cassette 12 into the collection bag to remove air from the fluid flow channel during initial setup and during operation of the infusion system.

A cassette-locked-in-place sensor 38 is operative to provide a signal that represents that the cassette is in its intended operating position to prevent fluid leakage and unintended infusion.

A pressure transducer 40 is operatively connected to the pressure chamber 22. The pressure transducer 40 is operative to provide an analog signal representative of the pressure in the pressure chamber 22. An amplifier 42 amplifies the analog signal, and an analog to digital converter (ADC) 44 converts the amplified analog signal into digital data. During preselected stages of a pumping sequence to be described, the digital data provides information representative of air in line, of actual infusion volume relative to nominal infusion volume, of patient output line occlusion, and of fluid level remaining to be infused through corresponding fluid input ports 16.

A pumping actuator 46 is operatively connected to the pump chamber 20. The pumping actuator 46 is operative to controllably fill and pump fluid from the pumping chamber 20 into either the patient output port 26 or the vent output port 30 in dependence on the state of actuation of the valves 28 and 32. The pumping actuator 46 is operative to precisely administer an intended amount of fluid in an intended time interval from any one or more of the fluid input ports 16 in any order either in time sequence or in time overlap to dilute the concentration of a selected infusate.

A system controller generally designated 48 is operatively connected to the input and output valve actuator 34, to the vent valve actuator 36, to the cassette-locked-in-place sensor 38, to the analog to digital converter 44, and to the pumping actuator 46. The system controller 48 is operative to provide control signals to the actuator 34 to "open" and "close" the valves 28 in an intended time sequence, to provide control signals to the actuator 46 to pump the chamber 20 at a rate selected to administer a preselected volume of infusate during a prescribed time interval, and to provide control signals to the actuator 36 to eliminate air from the fluid flow path during set-up and during infusion.

An operator interactive display 48A is operatively connected to the system controller 48. The display 48A is operative to display one of plural display templates that individually correspond to the modes of operation of the system controller 48, to display system status information, to display operator prompts to assist the operator in selecting volume, rate, and time of infusion, and to display various error and alarm conditions. The modes include a flush mode template, a prime mode template, an override mode template, a primary mode template, and a piggyback mode template.

Operator data and function keys 48B are operatively connected to the system controller 48. The data and function keys 48B are operative for selecting the rate, volume, and time of infusion; for selecting the state of operation of the infusion system including the override mode, the priming mode, and the normal-on mode; for controlling the operator interactive display; and for selecting maximum occlusion pressure, minimum infusion rate, and total fluid volume to be administered.

Status light emitting diodes (LED's) 48C are operatively connected to the system controller 48. The LED's 48C are operative to provide a visual indication of the various alarm conditions and of battery status. An audible alarm 48D is operatively connected to the system controller 48 to provide an audible indication of alarm condition. One or more slave interfaces 48E are operatively connected to the system controller 48. Each slave interface 48E is connectable to an auxiliary pump that may be slaved to the system controller 48 to administer the infusion of an incompatible infusate. A universal asynchronous receiver transmitter interface (UART) 48F is operatively connected to the system controller 48. The UART 48F may be connected to any suitable peripheral device such as a display terminal or a computerized central nurse station.

A rectifier and regulator 50 are connected to a source of AC power 52 such as a conventional hospital outlet via a fusible link 54. A regulator 56 is connected to the rectifier and regulator 50 via a switch 59. The rectifier and regulator 50 and regulator 56 provide power to the infusion system in normal operation. A battery 58 provides power to the infusion system either in the event of a power failure or in the event that it is desirable to move the patient such as between an intensive care unit and an operating room. The battery 58, the rectifier and regulator 50, and regulator 56 are operatively connected to the ADC 44 designated "Voltage Inputs". The system controller 48 is operative in response to a fall in the output of the converter signal from the regulators below a predetermined value to switch to the battery 58, and the controller 48 is operative to activate a corresponding status LED to provide a low battery indication whenever the level of the battery falls below a predetermined level.

Figure 2:
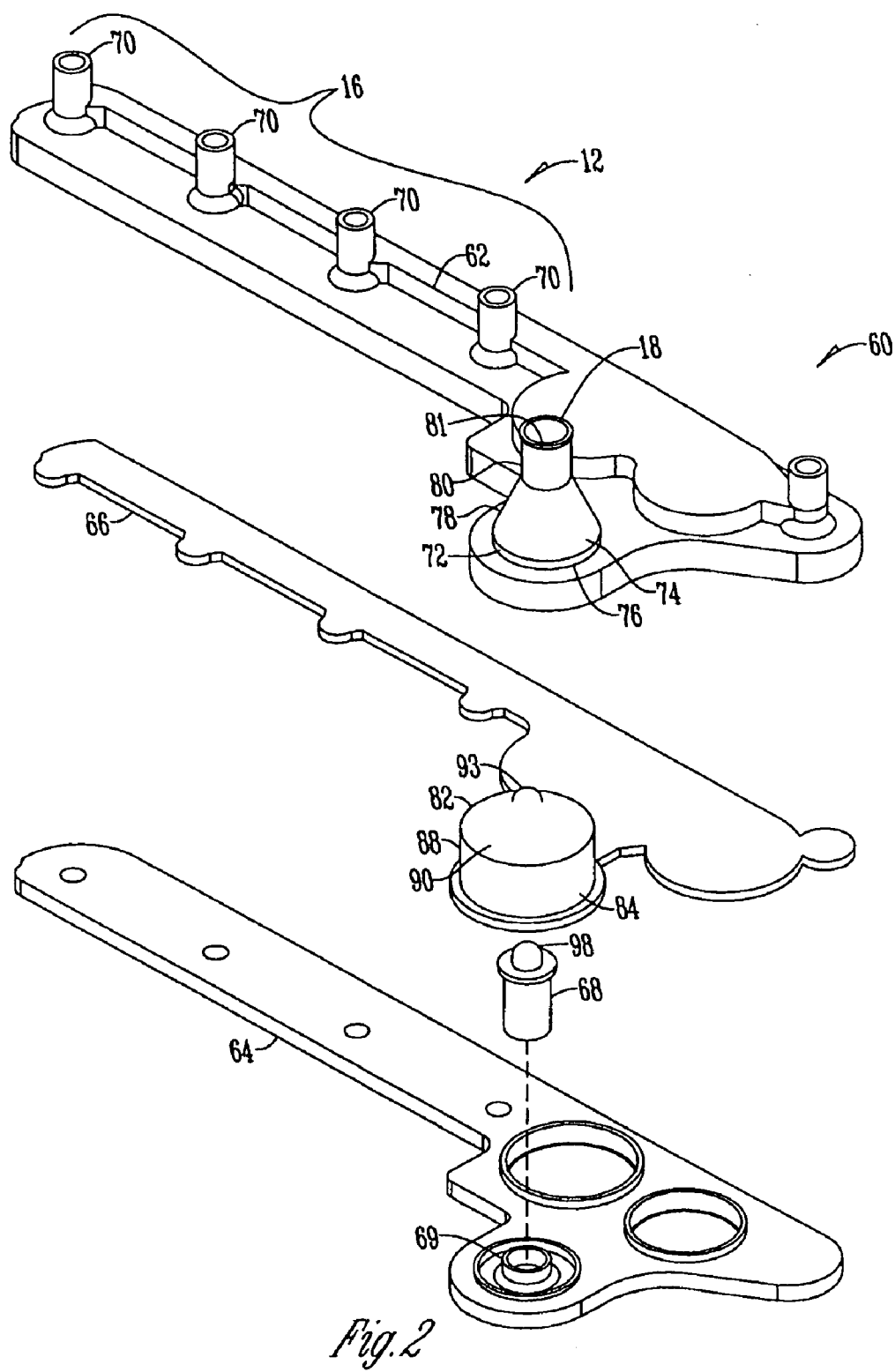
FIG. 2 is an exploded assembly view of a cassette according to the present invention.
Figure 3:
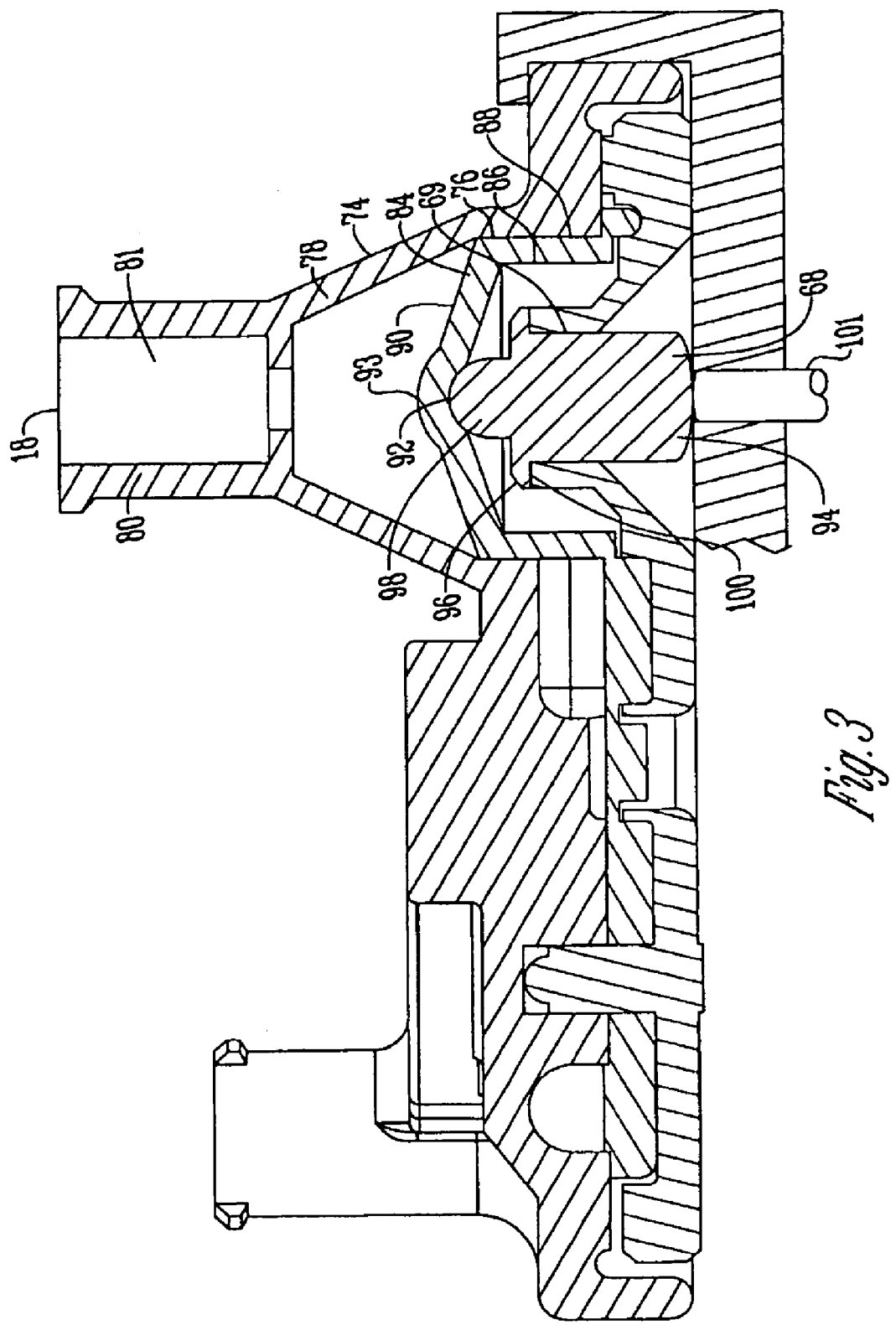
FIG. 3 is a side sectional view of the cassette installed in a pump and shows a valve in its normally closed position.
Figure 3A:
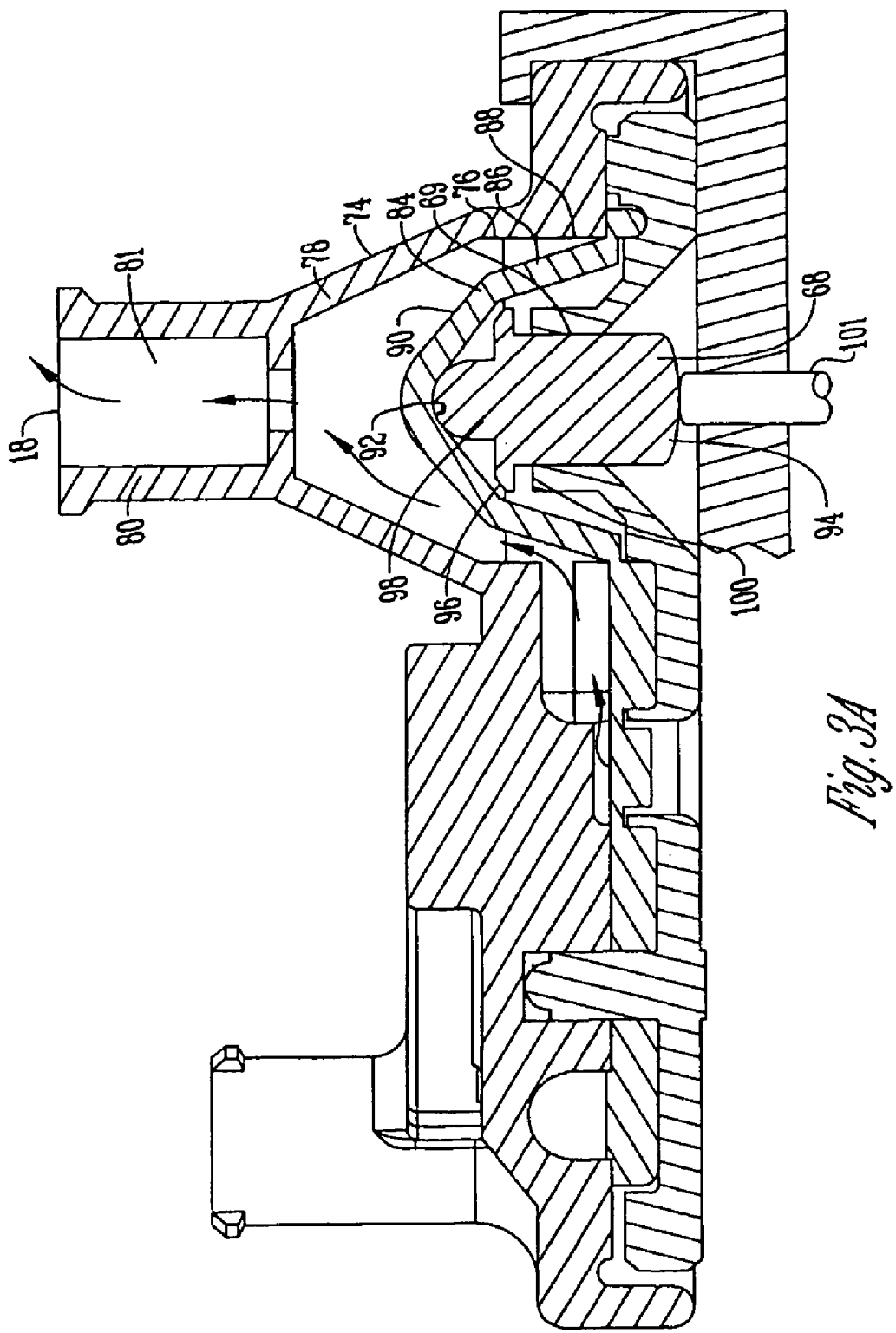
FIG. 3A is a side sectional view of the cassette of FIG. 3, but shows the valve in an open position.

FIGS. 2-3A show one embodiment of cassette 12. Cassette 12 comprises a cassette housing 60 having a first portion 62 and a second portion 64 that is considered a cassette cover. Sandwiched between the first and second portions 62, 64 of cassette 12 is a cassette diaphragm 66 that in one embodiment is an elastomeric membrane. The cassette 12 also comprises an actuating member 68 that sits within the cassette diaphragm 66. More particularly, the actuating member 68 is adapted to extend through an opening 69 in the second portion 64 of the cassette 12 and engages the diaphragm 66.

The first portion 62 of cassette housing 60 contains one or more inlet ports 16, such as a plurality of ports 70, which allow fluid flow into and within the cassette depending on internal valving. The first portion 62 of the cassette housing 60 also includes an outlet port 18. The outlet port 18 includes an outlet valve opening 72 that is defined by a sidewall 74 surrounding a cylindrical cavity 76, a conically shaped cavity 78, and an outlet portion 80 with a fluid passage 81 therein for fluid flow to a patient. Specifically, the cylindrical cavity 76 has a diameter wherein the conically shaped cavity 78 tapers upwardly and inwardly toward the outlet portion 80 to reduce the diameter of the cylindrical cavity 76.

The cassette diaphragm 66 has a valve 82 formed thereon. Specifically, the valve 82 in one embodiment is a raised cup or dome valve having a cupped member or dome 84 with a hollow interior 86 surrounded by a sidewall 88 that extends upwardly to a top portion 90. The top portion 90 tapers upwardly and inwardly. Optionally, an indentation 92 can be provided on the underside or lower surface of the top portion 90. The indentation can be centrally located in one embodiment, as shown. Also, an optional protrusion 93 can be provided on the upper or outer surface of the top portion 90 opposite the indentation 92 in order to maintain uniform wall thickness. The dome or cup member 84 has a diameter and thus cross section greater than that of the cylindrical cavity 76 such that when the cassette diaphragm 66 is sandwiched between the first and second portions 62, 64 of the housing 60 the valve is forced radially against the sidewall 74 of the outlet valve opening 72 occluding the fluid path through the opening 72. Thus, the valve 82 is in a normally closed position.

The actuating member 68 has a cylindrical body 94 with an annular shoulder 96 extending therefrom. The cylindrical body 94 extends from a first end to a second end terminating in a protrusion 98 adjacent the annular shoulder 96. Specifically, the protrusion 98 matingly fits within the centrally located indentation 92 of the dome 84 to align the actuating member 68 with the valve 82. Additionally, the cylindrical body 94 extends through an opening 69 in the second portion 64 of the housing 60 and the annular shoulder 96 rests upon a seat 100 to allow the actuating member 68 to sit within the second portion 64 of the housing 60. Therefore when disconnected from the pump the resilience of the diaphragm 66 will bias the actuating member 68 into a position in which the annular shoulder 96 rests upon the seat 100 to retain the actuating member.

One skilled in the art will appreciate that the geometry of the outlet port 18, the valve opening 72, the valve 82, the actuating member 68, and opening 69 can be non-cylindrical as well. The mating parts need only be complementary in shape. For example, the valve opening 72 of the outlet port 18 and the valve 82 may be oval, square, prismatic, pyramidal, or other shapes without significantly detracting from the invention, although the cylindrical shape has been chosen for ease of manufacturing. Of course, the spread of the valve 82 should be greater than the spread of the opening 72 of the outlet port. The actuating member 68 and opening 69 can be almost any polygon or curved shape.

In a preferred embodiment wherein the actuating member 68 is a push rod, when the cassette 12 is connected to the pump 10 a pin 101 from the pump engages the push rod to move the annular shoulder 96 off of the seat 100 to engage the valve 82 for actuation. When disconnected from the pump the push rod 68 can be manually operated to prime the tubing set outside of the pump 10.

In operation, when the cassette 12 is locked into the pump 10 a plurality of pins (not shown) of the pump are advanced into the cassette 12, as described in U.S. Pat. No. 4,865,584. The plurality of pins advance into the underside of the cassette membrane or diaphragm 66 to close the inlet and outlet valves of the cassette 12, as described in U.S. Pat. No. 4,865,584. At this point the pump 10 can control the opening and closing of the ports to control fluid flow within the cassette.

Simultaneously, an anti-free flow pin 101 from the pump engages the actuating member 68 to move the actuating member 68 axially to open the valve 82. Once engaged the movement of the anti-free flow pin 101 causes the valve 82 to expand axially and thus contract the sidewall 88 radially away from the sidewall 74 of the opening 72 to open the fluid path through the cavity 76. Thus, when the cassette 12 is securely attached to the pump, fluid is allowed to flow through the cassette 12 from inlet 16 to outlet 18 to the patient under the control of the pump.

When the cassette 12 is unlocked from the pump 10 the plurality of pins (not shown) are retracted from the underside of the cassette membrane to open the inlet and outlet valves. Simultaneously the anti-free flow pin 101 retracts, releasing the external force on the actuating member 68, which allows the valve 82 to resiliently move back to its original position wherein the valve occludes the outlet valve opening 72. Therefore, at no time is there uncontrolled free flow through the cassette 12.

Figure 4:
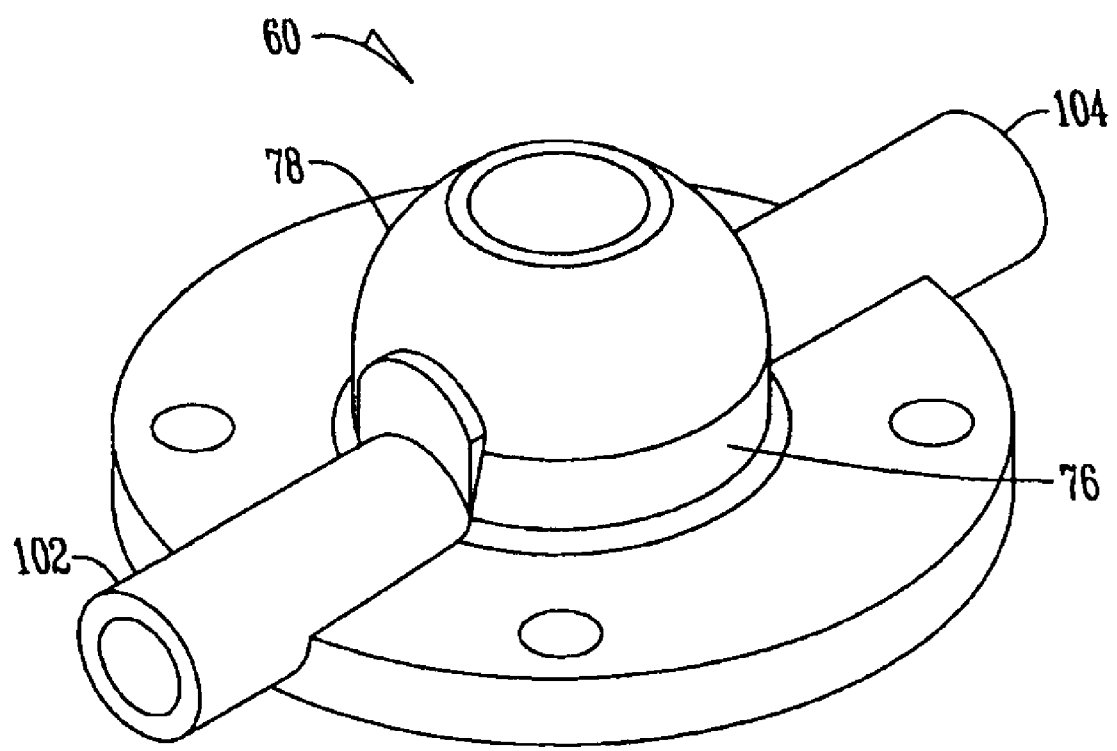
FIG. 4 is a perspective view of an alternative embodiment of the valve.
Figure 4A:
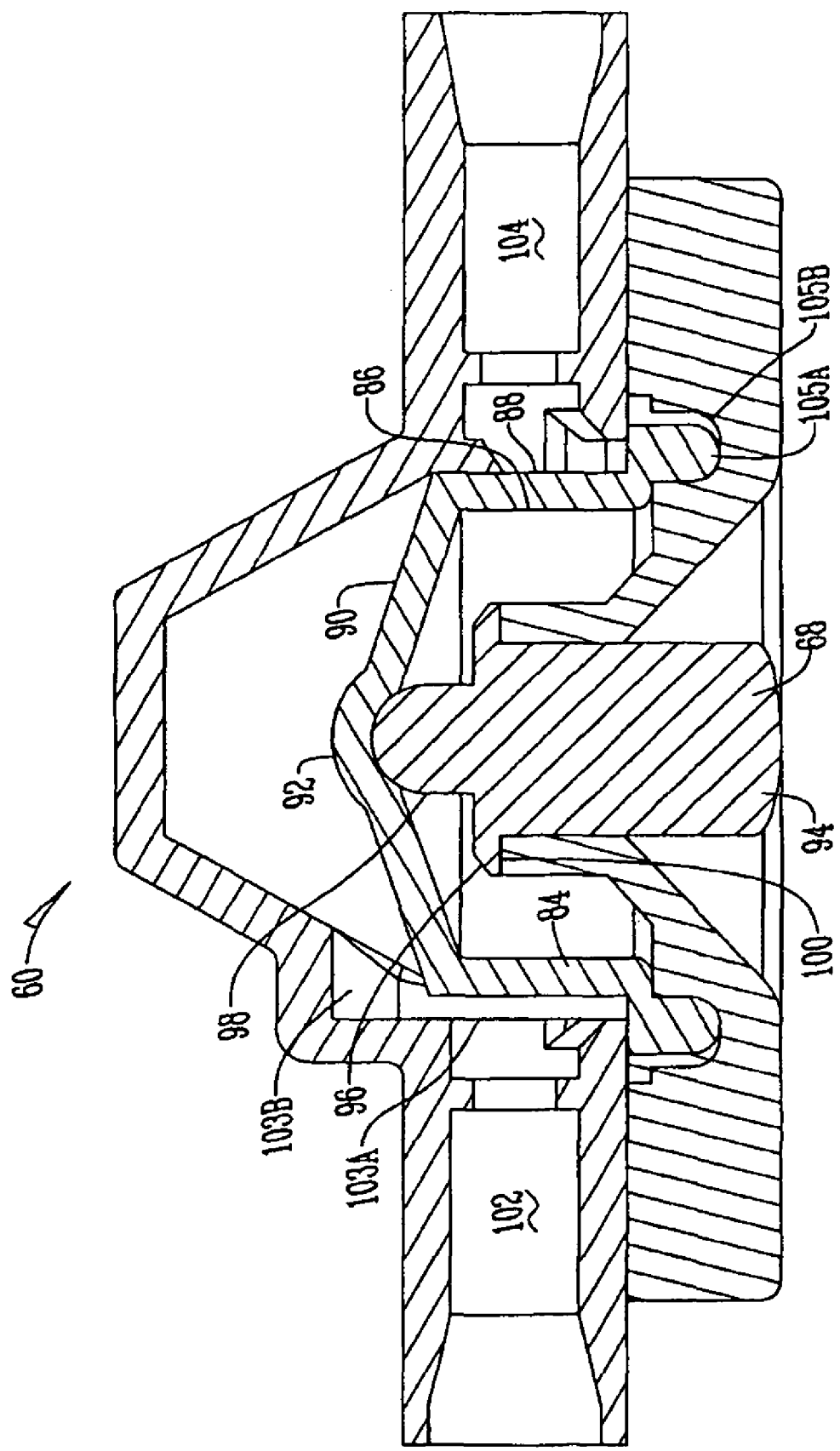
FIG. 4A is a side sectional view of the valve of FIG. 4 and shows the valve in its normally closed position.
Figure 4B:
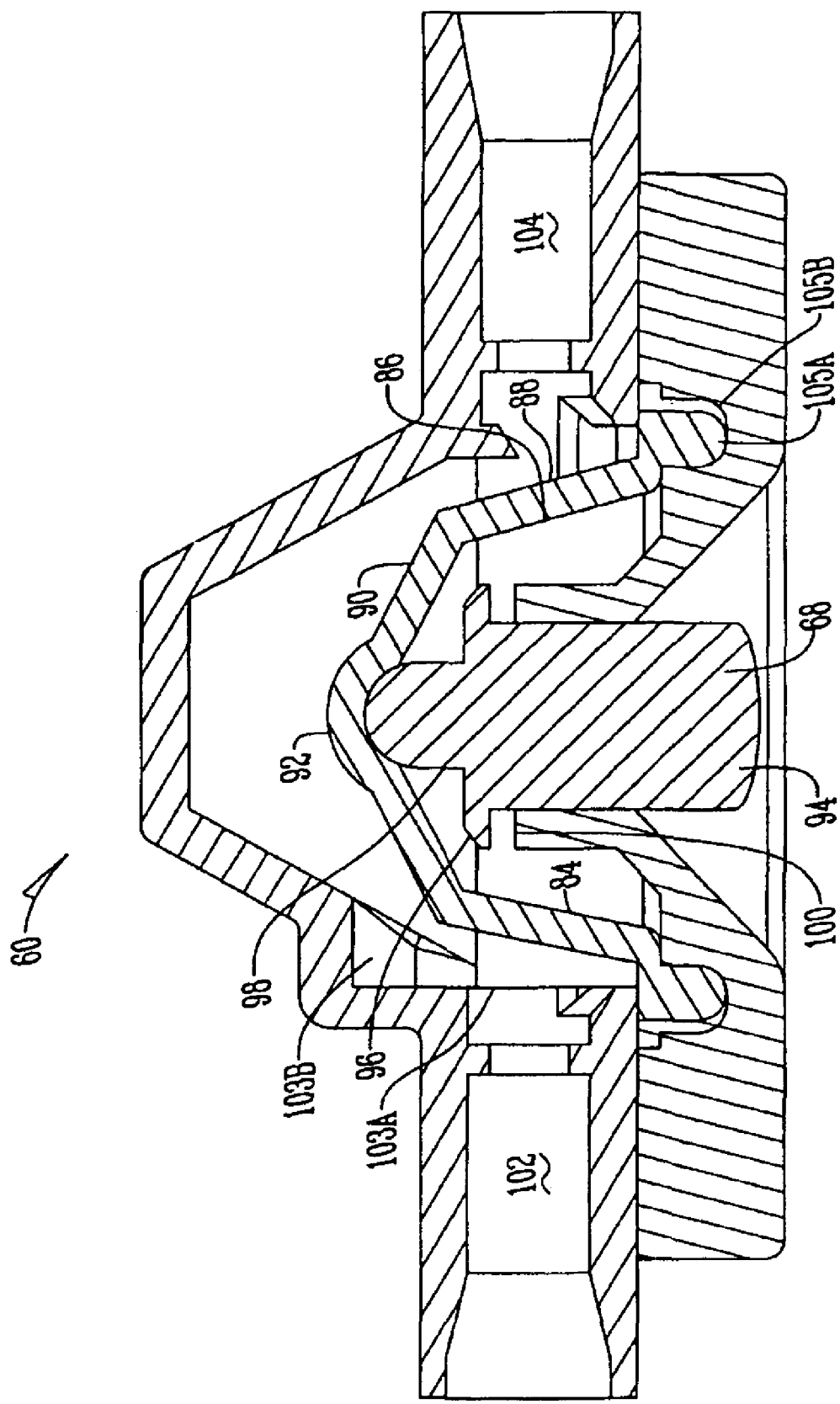
FIG. 4B is a side sectional view of the valve of FIG. 4, but shows the valve in an open position.
Figure 5:
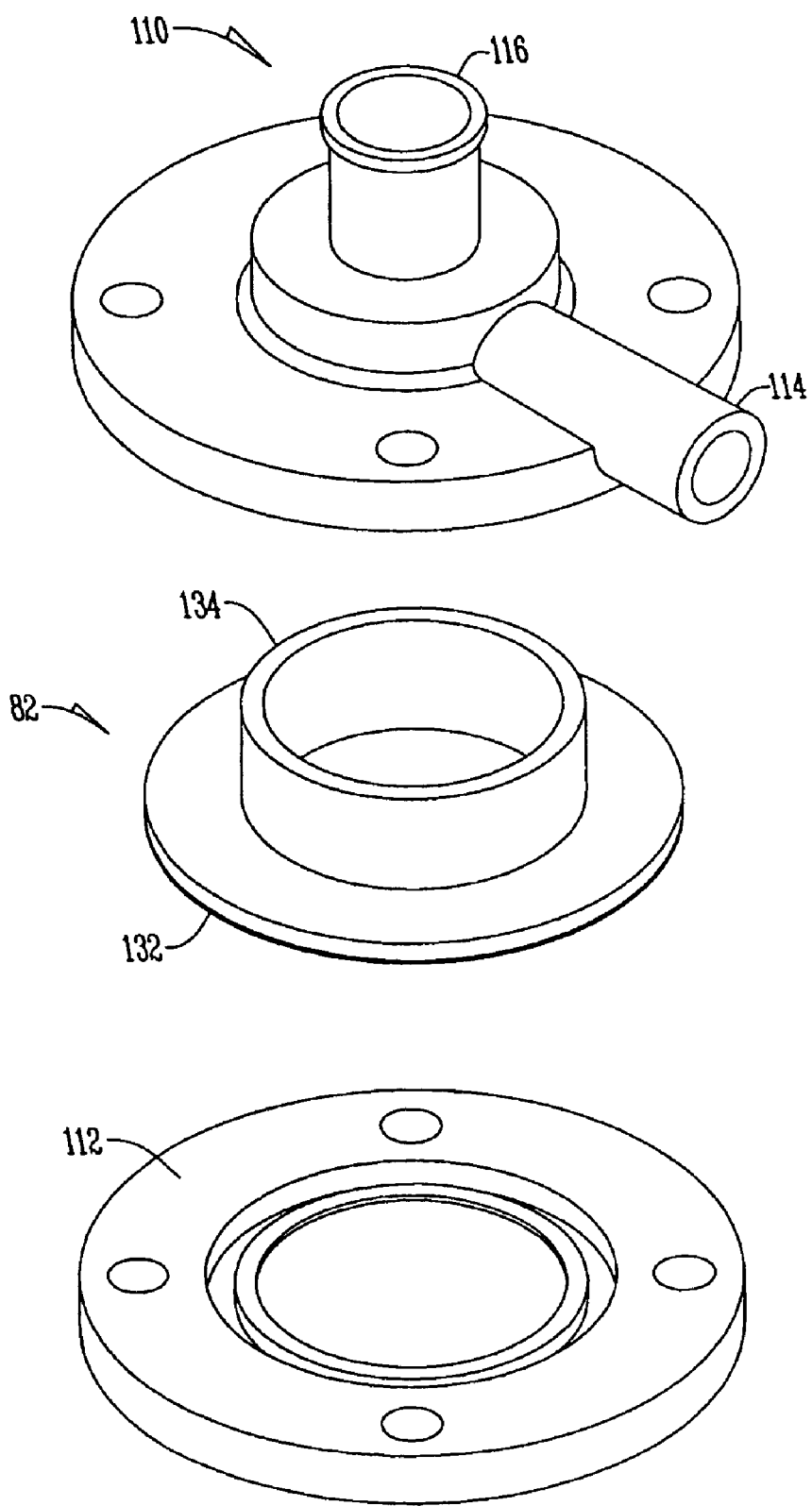
FIG. 5 is an exploded assembly view of portions of an alternative embodiment of a valve assembly.
Figure 6:
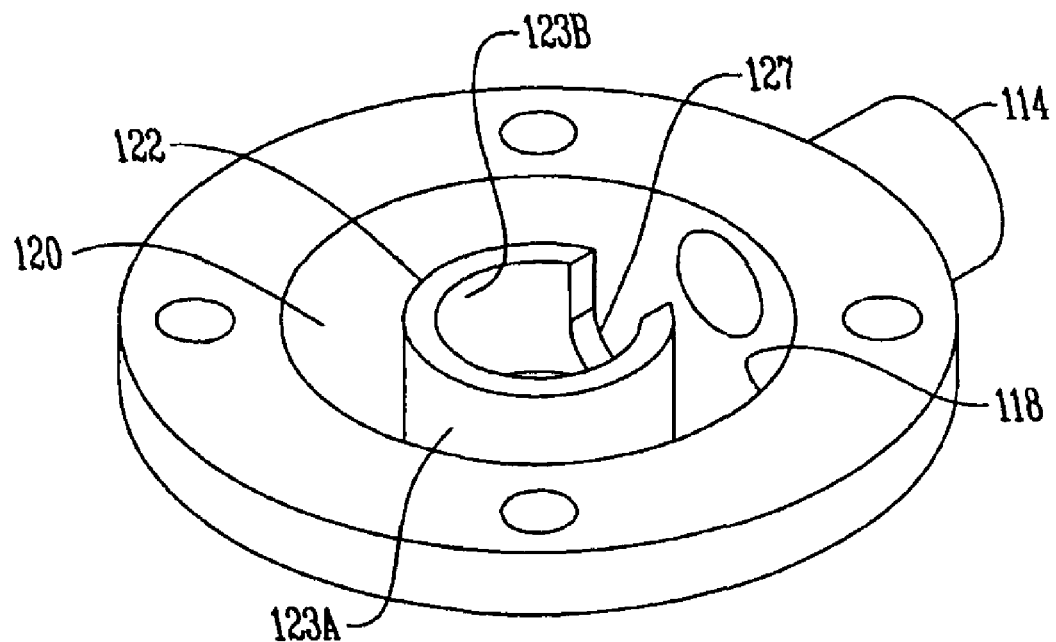
FIG. 6 is a bottom perspective view of a valve body.
Figure 7:
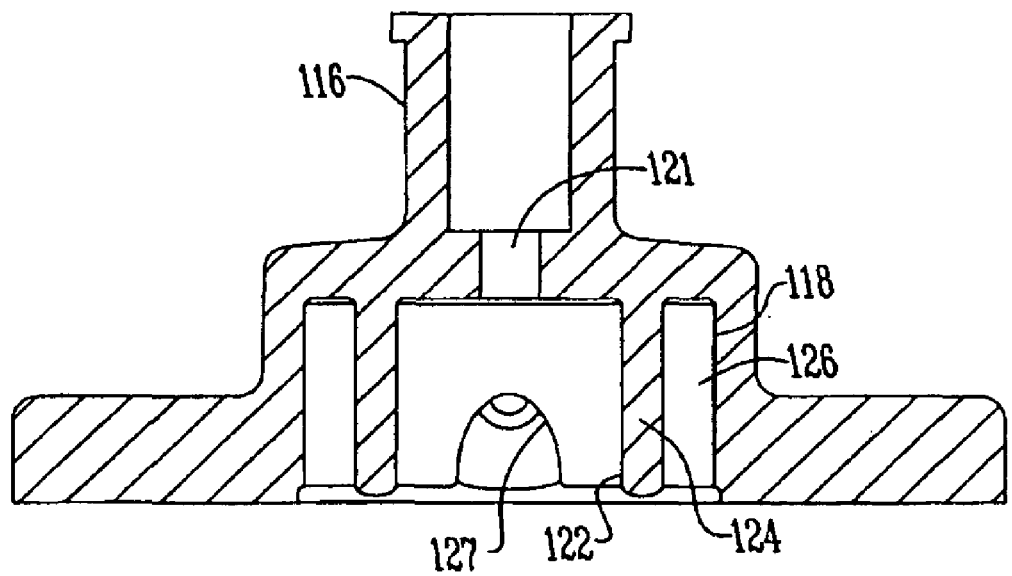
FIG. 7 is a sectional view of a valve body.
Figure 8:
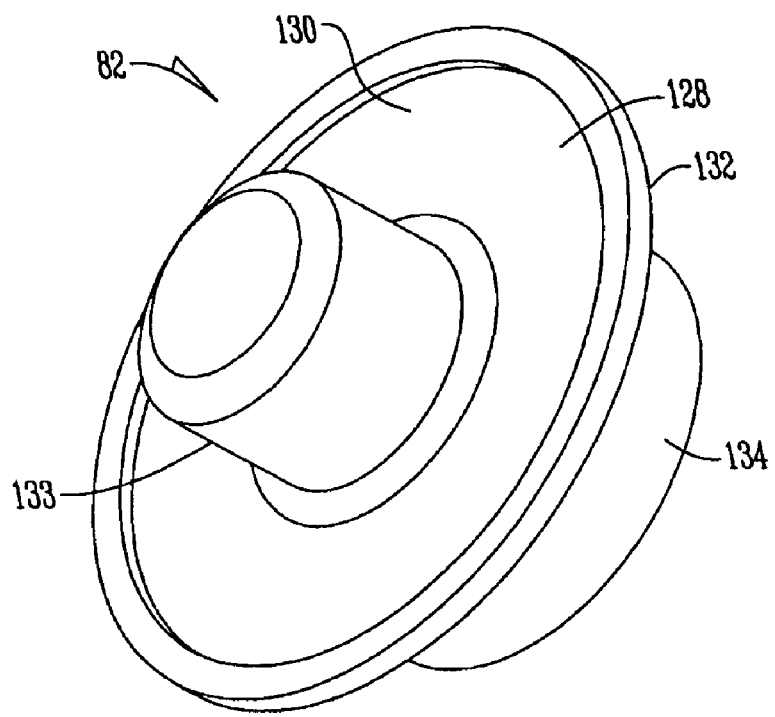
FIG. 8 is a perspective view of a diaphragm.

FIGS. 4-4B show an alternative embodiment wherein the valve 82 can operate as a check valve. Specifically the housing 60 has a first port 102 in fluid communication with the sidewall 88 and top portion 90 of valve 82 through a chamber opening 103A and chamber 103B. A second port 104 is also in fluid communication with the sidewall 88 of valve 82. The first port and second port 102 and 104 are spaced apart and in one embodiment can be generally aligned and on opposite sides of the valve 82. In this embodiment, as in the previous embodiments, the sidewall 88 of valve 82 extends into a lip portion 105A that is retained within a groove 105B between the first and second portions 62 and 64 of the cassette 12. When actuated by an actuating member 68 the lip portion 105A is held within groove 105B allowing the sidewall 88 to contract radially.

Thus, when fluid pressure is applied to the first port 102 the pressure is transmitted immediately through the chamber opening 103A and the chamber 103B to a top surface of the top portion 90 of the valve 82, which urges the top portion 90 downwardly and outwardly to radially expand the sidewall 88, tending to increase the strength of the seal. When pressure is applied to the second port 104 the valve 82 opens upon reaching a threshold pressure. The threshold pressure is the cracking pressure of the valve 82 in this embodiment.

Thus, in the embodiment of FIGS. 4-4B, the valve 82 acts as a pressure activated check valve allowing flow from the second port 104 into the cylindrical cavity 76 if above the threshold cracking pressure and resisting flow from the first port 102. Therefore, actuating member 68 and/or the pin that 101 engages the actuating member 68 may be omitted or used as an auxiliary means of opening the valve. Alternatively, when the actuating member 68 and/or the pin 101 are included and their position and/or biasing force is adjustably controlled, the cracking pressure of the valve can be adjusted and the valve 82 functions as a pressure-relief valve.

U.S. Pat. No. 5,718,569 provides a valve similar to the valve and cover shown in FIGS. 5-10B. The entire disclosure, including figures, of the '569 patent is specifically incorporated by reference herein. Specifically, the '569 patent teaches an anti-free flow valve that is given the numeral "64" therein. The valve of FIGS. 5-10B is an improvement over this '569 valve.

Referring to FIGS. 5-10A a cupped diaphragm or valve 82 is shown that fits within a valve body 110 similar to first housing portion 62 of the present disclosure and is covered by a valve cover 112 similar to the second housing portion 64 of the present disclosure. The valve body 110 and valve cover 112 can be fastened together by conventional methods such as ultrasonic welding, heat welding, screws or similar fastening means. In one embodiment, the valve of FIGS. 5-10B of the present disclosure functions similarly, albeit inversely in some respects, to the radially sealing cupped member described above in the embodiments of FIGS. 2-4B of the present disclosure.

The valve body 110 has an inlet port 114 and an outlet port 116 to provide fluid flow therethrough. The valve body 110 has an interior sidewall 118 that surrounds a cavity 120 therein. The cavity 120 can be centrally located as shown or offset without detracting from the invention and is fluidly connected to the outlet port 116 via outlet valve passage 121. Within the cavity 120 is a port fitting 122 having a sidewall 124 that is disposed within the interior sidewall 118 to define a passageway 126 between the sidewalls 118 and 124 within cavity 120. The port fitting 122 has an outer surface 123A and an inner surface 123B. The port fitting 122 can be cylindrical and then the passageway 126 is annular in one embodiment, as shown. However, other shapes will not detract from the invention. As seen in FIG. 6-10B, a fluid passage 127 (in the form of a hole or notch) extends through the port fitting 122 to fluidly connect the cavity 120 and passageway 126 with the outlet port 116.

As best seen in FIGS. 8-10B, the diaphragm or valve 82 of this embodiment has a body 128 having a bottom portion 130 and top portion 132. The body 128 and its bottom portion 130 and top portion 132 can be circular, although other shapes complementary to the valve body 110 and valve cover 112 will not detract from the invention. The bottom portion 130 has a protrusion 133 extending therefrom. The protrusion 133 can be a variety of shapes without detracting from the invention. In one embodiment the protrusion 133 is circular and has a diameter less than the diameter of the body 128.

Extending from the top portion 132 is an annular flange 134. Specifically the annular flange 134 and circular body 128 form a hollow cupped member or dome portion 136 having an interior 138 surrounded by the annular flange 134. The annular flange 134 is placed within the annular passageway 126 or cavity 120 of the valve body 110 to engage and surround the sidewall 124 of cylindrical port 122. The inner diameter or profile of the flange 134 is less than the outer diameter of the port fitting 122, so that the valve 82 normally frictional engages and thereby seals against the outer surface 123A of the port fitting 122, preventing fluid flow communication through passageway 126 and the passage 127. Again, while elements within the description describe circular elements, other shapes are contemplated and are within the scope of this disclosure.

Figure 9:
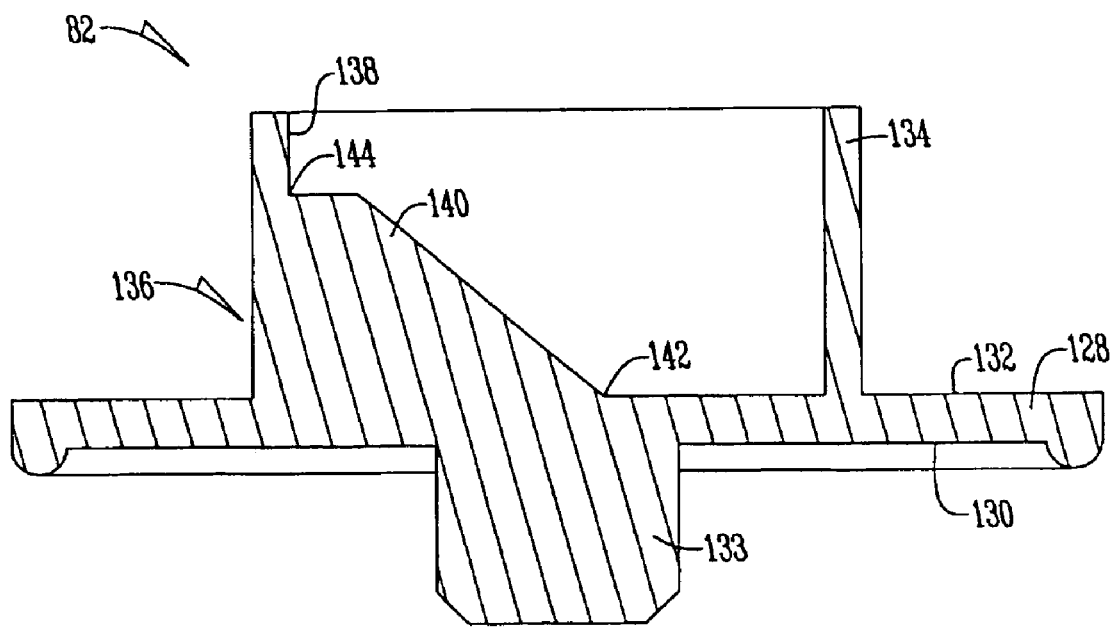
FIG. 9 is a sectional view of a diaphragm.
Figure 10:
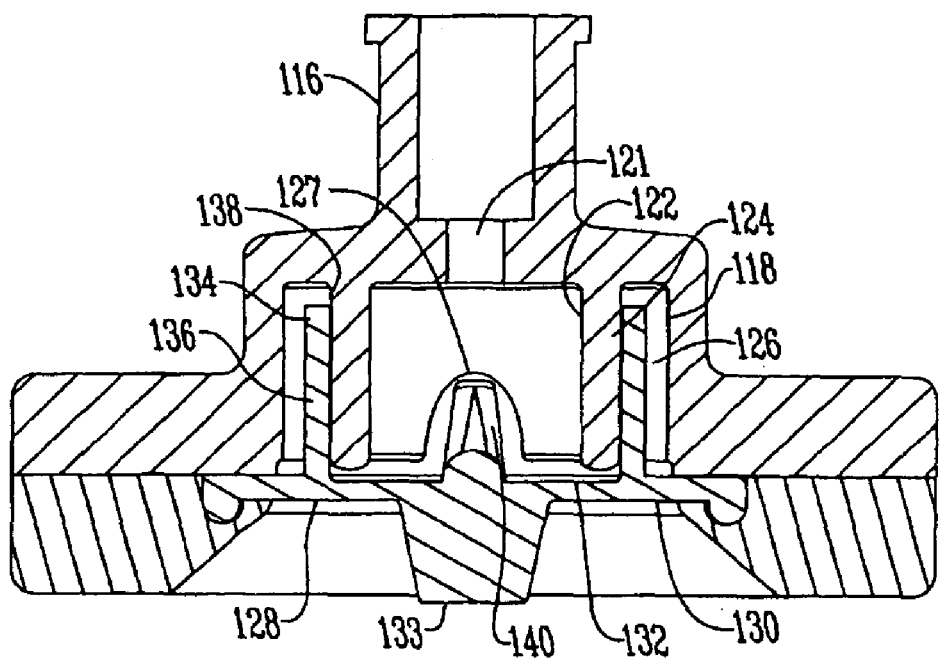
FIG. 10 is a sectional view of a valve assembly in its normally closed position.
Figure 10A:
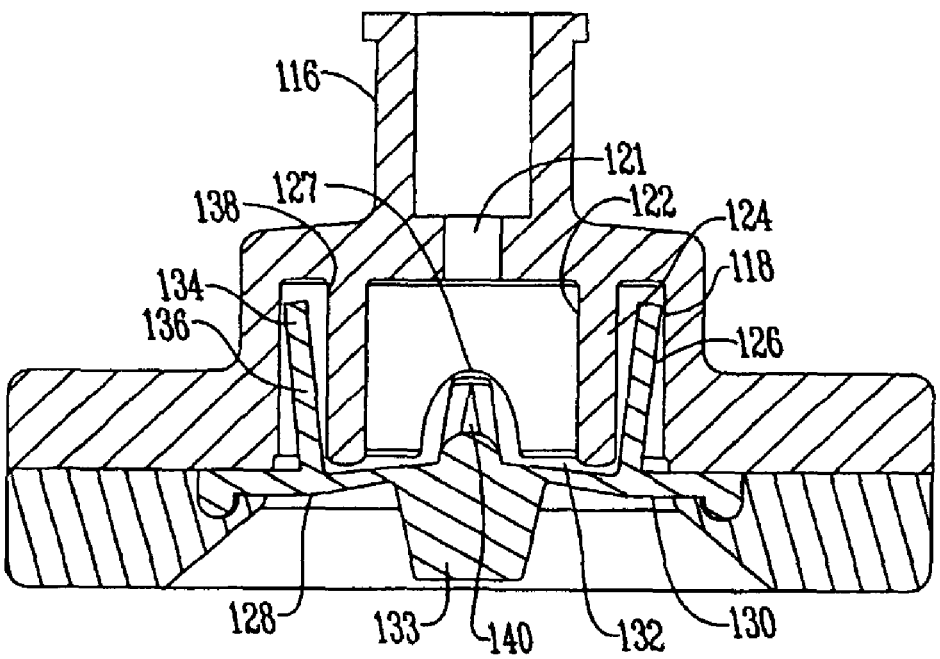
FIG. 10A is a sectional view of the valve assembly of FIG. 10, but shows the valve assembly in an open position.
Figure 10B:
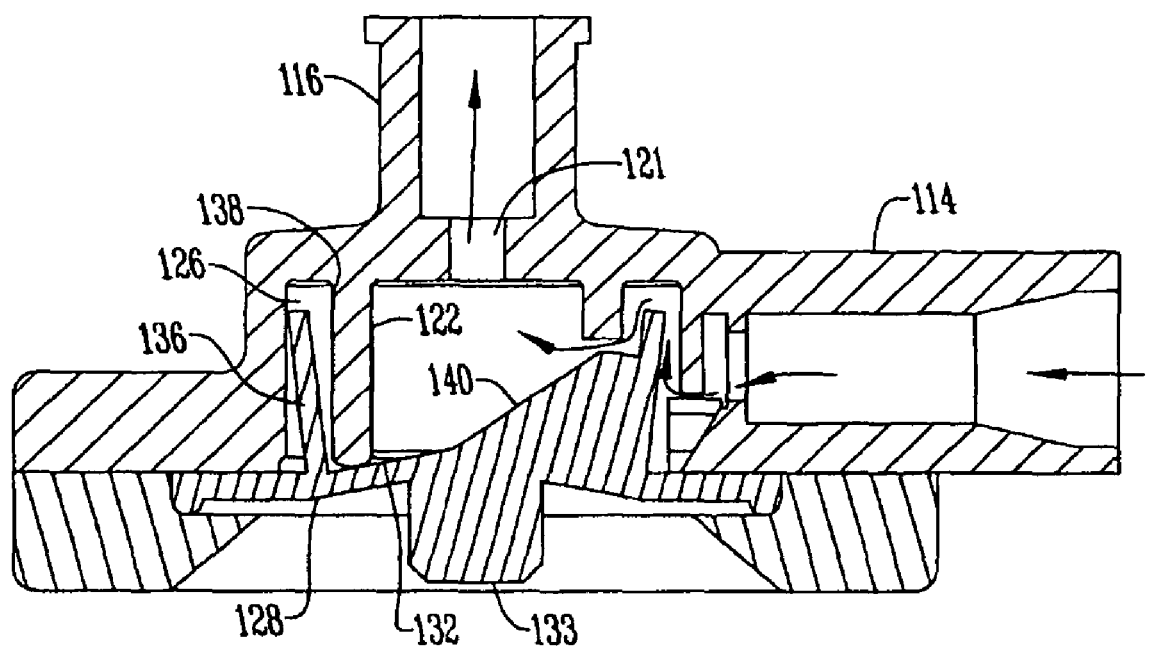
FIG. 10B is a sectional view of the valve assembly of FIG. 10, but shows the valve assembly in an open position.

As best seen in FIGS. 9 and 10B, disposed within the interior 138 and attached to the annular flange 134 is a gusset 140. Gusset 140 has a triangular cross-section and extends diagonally from a first end 142 adjacent the underside of the protrusion 133 to a second end 144 that terminates into the annular flange 134 on a plane parallel to the bottom portion 132 of the annular body 128. Gusset 140 registers with the fluid passage or notch 127. Gusset 140 provides structural support, alignment, and acts to focus or direct external force from an actuating member 68.

In operation, similar to the embodiments shown in FIGS. 2-4B, the annular flange 134 resiliently occludes the notch 127 to prevent fluid flow through valve body 110 in a normally closed position as shown in FIG. 10. When locked to the pump a pin 101 (FIG. 3A) of the pump is aligned with the axis of the valve 82 to engage the circular protrusion 133 of valve 82. Once engaged the pin 101 moves the circular protrusion 133 toward the interior 138 of the annular flange 134 via gusset 140, causing the annular flange to expand radially. The radial expansion separates the annular flange 134 from the sidewall 124 of the cylindrical port 122 to open fluid flow through the valve body 110 via annular passageway 126 and notch 127, as shown in FIGS. 10A and 10B. When the pin 101 is retracted the valve 82 returns to its original shape, closing the fluid path. Alternatively, the valve 82 can be manually actuated or opened as described above by the user applying external force in an axial direction on the upper portion 130 or the protrusion 133. The user can prime an infusion set containing the valve 82, with or without the aid of the pump.

Compared to the valve of FIGS. 2-3A the advantage of the valve of FIGS. 5-10B is that pressure in the direction of forward flow tends to make this valve seal more tightly. Additionally, an extra actuating member 68 or push rod is needed in the embodiments of FIGS. 2-4B. Thus the valve of FIGS. 5-10B eliminates parts and costs as compared to the valves of FIGS. 2-4B. Additionally, one can also adjust the strength of seal by selection of dimensions for tighter frictional fit.

Therefore, disclosed is a normally closed, radially sealing anti-free flow valve 82 and cassette 12 that prevents fluid flow when disengaged from a pump 10. Specifically, in one set of embodiments a cupped or raised dome valve having a greater outside diameter than the diameter of a cylindrical cavity in the cassette housing occludes or closes a fluid path through the inlet port and outlet port of the cassette. Then, when locked to a pump an actuating member causes the valve to radially contract causing the flow path to be opened.

In another embodiment, the cupped valve is inverted and has a smaller inside diameter than the outer diameter of an outlet port fitting so as to normally occlude or close a fluid passage therethrough. The valve is opened by applying a force in an axial direction on the top of the cup or a protrusion extending therefrom, which urges the sidewall of the cup radially outward to unseal the sidewall from the port fitting.

Therefore, provided is a simple and economical design for a valve and a cassette incorporating various embodiments of such a valve that adds minimal components to known cassettes. The integrity of the seal from the valve is robust, well controlled and easily manufactured. In one embodiment, the valve simply needs to have a larger diameter than the opening of the cavity wherein the valve to occlude the opening. In another embodiment, the valve simply needs to have a smaller inside diameter than the diameter of an outlet port fitting to fit over and occlude a fluid passage in the fitting. Additionally the parts can be made self centering or aligning and thus cracking pressure is not dependent on precise control of the alignment of the parts during assembly. This in turn reduces manufacturing costs and complications. Thus, at the very least all of the stated objectives have been met.

It will be appreciated by those skilled in the art that other various modifications could be made to the device without departing from the scope of this invention. All such modifications and changes fall within the scope of the claims and are intended to be covered thereby.

What is claimed is:

1. A cassette for use in a pump that delivers a medicinal fluid, comprising:
   a housing having an inlet port through which the medicinal fluid enters the cassette and an outlet port through which the medicinal fluid leaves the cassette, said housing providing a sealed fluid path between the inlet port and the outlet port;
   an elastomeric membrane disposed within the housing and cooperating with the housing to define the fluid path between the inlet port and the outlet port;
   a valve being disposed in the fluid path between the inlet port and the outlet port;
   said valve having a hollow cup having an interior surrounded by an annular flange;
   said annular flange engaging and surrounding a sidewall of a cylindrical port within a valve body to close the fluid path;
   an actuating member engaging the hollow cup axially such that when actuated the annular flange expands radially to open the fluid path; and
   wherein a gusset is disposed within the interior of the hollow cup and is attached to the annular flange.

2. The cassette of claim 1 wherein the valve has a protrusion wherein the actuating member engages the protrusion to open the fluid path to allow manual actuation of the valve.

3. The cassette of claim 1 wherein the actuating member is a pin.

* * * * *